United States Patent
Mimoun et al.

(10) Patent No.: US 6,806,250 B2
(45) Date of Patent: Oct. 19, 2004

(54) USE OF FATTY ALCOHOL IN A PERFUME COMPOSITION

(75) Inventors: Hubert Mimoun, Challex (FR); Günter Holzner, Grand-Lancy (CH); Joël Pastori, Grand-Lancy (CH)

(73) Assignee: Firmenich SA, Geneva (CH)

( * ) Notice: Subject to any disclaimer, the term of this patent is extended or adjusted under 35 U.S.C. 154(b) by 126 days.

(21) Appl. No.: 10/115,485

(22) Filed: Apr. 2, 2002

(65) Prior Publication Data

US 2002/0183236 A1 Dec. 5, 2002

Related U.S. Application Data

(63) Continuation of application No. PCT/IB00/01499, filed on Oct. 19, 2000.

(51) Int. Cl.$^7$ ................................................. A61K 7/46
(52) U.S. Cl. ............................................................ 512/1
(58) Field of Search ............................................... 512/1

(56) References Cited

U.S. PATENT DOCUMENTS

| 3,888,995 A | * | 6/1975 | Katz et al. ................... 514/772 |
| 5,190,915 A | | 3/1993 | Behan et al. ................... 512/2 |
| 5,324,444 A | | 6/1994 | Berry et al. ................... 252/174 |
| 5,420,104 A | | 5/1995 | Holzner et al. ................. 512/2 |
| 5,525,588 A | * | 6/1996 | Michetti .......................... 512/4 |
| 5,831,133 A | | 11/1998 | Mimoun ......................... 568/814 |
| 6,099,858 A | * | 8/2000 | Morton et al. ................ 424/456 |
| 6,368,607 B1 | * | 4/2002 | Rerek et al. ................... 424/401 |
| 6,444,212 B1 | * | 9/2002 | Cavazzuti et al. ............ 424/401 |

FOREIGN PATENT DOCUMENTS

| EP | 0 701 813 A2 | 3/1996 |
| JP | 61151114 | 7/1986 |
| WO | WO 96/37285 | 11/1996 |
| WO | WO 97/01326 | 1/1997 |
| WO | WO 99/12877 | 3/1999 |

* cited by examiner

*Primary Examiner*—Jill Warden
*Assistant Examiner*—Monique T. Cole
(74) *Attorney, Agent, or Firm*—Winston & Strawn LLP

(57) ABSTRACT

The invention concerns a fatty alcohol obtainable by a method which consists in reducing the carbonyl function of a vegetable or animal oil, the method consisting in reacting said vegetable or animal oil with appropriate amounts of polymethylhydroxysiloxane (PMHS) in the presence of a catalytic system prepared from a metal salt or complex and a reduction agent, followed by hydrolysis of the resulting siloxane with a basic agent and separating and purifying the desired alcohol thus formed. Said alcohol can be used in a perfume composition, in particular as solubilizing agent.

13 Claims, No Drawings

USE OF FATTY ALCOHOL IN A PERFUME COMPOSITION

CROSS-REFERENCE TO RELATED APPLICATIONS

This application is a continuation of the U.S. national Stage designation of International application PCT/IB00/01499 filed Oct. 19, 2000, the entire content of which is expressly incorporated herein by reference thereto.

TECHNICAL FIELD

The present invention relates to the field of perfumery. More particularly, it relates to the use, in a perfuming composition, of a fatty alcohol obtainable by a process of reducing the carbonyl function of a vegetable or animal oil with appropriate quantities of polymethyl-hydroxysiloxane.

PRIOR ART

The use of fatty alcohols in cosmetic compositions is well known from the prior art, for example from patent application WO 96/37285, which discloses the use of fatty alcohols in emulsifying cosmetic compositions, or from application WO 97/01326, which describes cream compositions comprising in particular, from among the hydrophobic agents used, fatty alcohols. In this type of application, the fatty alcohols used act as a structurant in order to promote the Theological characteristics of the composition. More generally, the long-chain fatty alcohols are therefore used as emollients in cosmetic or pharmaceutical compositions, as structurants in emulsions or as stabilisers in an emulsifying system. They are frequently found in compositions for hair care products, in moisturising creams for dry skin and in pharmaceutical bases.

However, to our knowledge, these alcohols have never been used in perfuming compositions.

DESCRIPTION OF THE INVENTION

We discovered, quite surprisingly, that the fatty alcohols obtainable by reducing the carbonyl function of a vegetable or animal oil of natural origin could advantageously be used in perfuming compositions. In particular, and according to a preferred embodiment of the invention, these fatty alcohols can quite unexpectedly act as a solvent or co-solvent in these perfuming compositions.

The use of the fatty alcohols according to the invention in perfuming compositions, in particular as solubilisers of the perfuming ingredients which are a constituent of these compositions, has numerous advantages. In the preparation of perfumes, eaux de toilette and eaux de Cologne for example, the use of solvents such as ethanol or isopropanol is very common. Ethanol provides good solubilisation of the perfuming ingredients to which the perfumer has recourse. The perfumes and eaux de toilette found on the market generally contain between 50% and 95% ethanol by volume. However, this type of solvent commonly used in perfumes or other perfuming compositions can be subject to use restrictions by the legislation of certain countries. For this reason, the attempt is being made to replace this type of solvent in the aforementioned products. We have discovered that the fatty alcohols derived from vegetable or animal oils can advantageously replace, in whole or in part, the aforementioned solvents commonly used in perfumery. In fact, these products of natural origin easily solubilise any type of perfuming ingredient.

Other advantages will become apparent from the description and the examples.

The fatty alcohols according to the present invention are obtainable by reducing the carbonyl function of a vegetable or animal oil. This process consists in reacting the said oil with appropriate quantities of polymethylhydroxysiloxane (PMHS) in the presence of a catalytic system prepared from a metal salt or complex and a reducing agent, followed by hydrolysis of the resulting siloxane by means of a basic agent and the separation and purification of the desired alcohol thus formed. The precise process for the preparation of these alcohols is described in U.S. Pat. No. 5,831,133 and in International patent application WO 99/12877. The first of these documents describes e.g. an original process for the reduction of, in particular, esters by polymethylhydroxysiloxane, catalysed by soluble hydrides of metals such as zinc, manganese or iron. PMHS is a cheap and abundant co-product in the silicone industry. Stable in air and water, it is particularly easy to use in any polyvalent reactor, whereas the use of hydrides such as $LiAlH_4$ and $NaBH_4$ used in "conventional" reductions necessitates working in a dry reactor which has been rendered inert.

One of the remarkable properties of this technology is that it allows the direct reduction of the vegetable and animal oils with excellent yields. This reaction is catalysed preferably by soluble zinc hydrides produced e.g. by reaction between a soluble zinc carboxylate and a hydrogen donor such as $NaBH_4$.

The process described in WO 99/12877 is also suitable for the preparation of the fatty alcohols used according to the present invention and it has the additional advantage of dispensing with the use of $NaBH_4$.

The contents of U.S. Pat. No. 5,831,133 and application WO 99/12877 and the teachings of these documents in relation to the reduction of the appropriate natural oils and the application of these processes to this reduction are included herein by reference.

These processes are advantageously used to prepare the fatty alcohols according to the invention because they enable the structure and the stereochemistry of the starting products, namely the vegetable or animal oils, to be preserved. In other words, if one compares the reduction described in the documents included herein by reference with the conventional catalytic hydrogenation commonly used for reduction of the fatty animal or vegetable oils, this latter necessitates their prior transesterification into the corresponding methyl ester and is carried out on a large scale under drastic temperature and pressure conditions, which affects the position and the stereochemistry of the double bonds and, consequently, the natural character of the product. In constrast, the processes described in U.S. Pat. No. 5,831,133 and WO 99/12877 enable these to be preserved, with the result that the reaction product, i.e. the fatty alcohol, has the same stereochemistry as the initial animal or vegetable oil, thus preserving its natural form, which represents a considerable advantage. We also discovered that the fatty alcohols thus obtained could have properties which are highly advantageous to the object of the invention.

The present invention thus relates to the use, in a perfuming composition, of a fatty alcohol obtainable by a process of reducing the carbonyl function of a vegetable or animal oil, said process consisting in reacting the said oil with appropriate quantities of PMHS in the presence of a catalytic system prepared from a metal salt or complex and a reducing agent, followed by hydrolysis of the resulting siloxane by means of a basic agent and the separation and purification of the desired alcohol thus formed.

Of the fatty alcohols used according to the invention, the preferred ones are those which constitute the product of the reduction of a vegetable oil selected from the group comprising olive oil, sunflower oil, palm oil, cottonseed oil, colza oil, soya oil, sesame oil, jojoba oil or coconut oil.

Apart from the fact that they preserve the position and the stereochemistry of the double bonds of the natural oils from which they are derived, the fatty alcohols according to the invention have further advantages when used in a perfuming composition. For example, these compounds impart to the composition to which they are added a soft, non-greasy feel when applied to the skin, whereas a conventional solvent such as ethanol has the tendency to dry out the skin.

The alcohols according to the invention are used to particular advantage not only in perfumes, eaux de Cologne and eaux de toilette, but also in applications such as perfumed oils for the skin or hair.

It goes without saying that the use of the fatty alcohols derived from vegetable or animal oils according to the invention is not limited to the aforementioned products, but is also suitable for other perfumery applications, in particular in functional perfumery. Examples of this type of application include shower and bath gels, shampoos, deodorants and anti-perspirants. Owing to their natural character, their emollient properties, their non-greasy nature, their softness to the touch and their penetration power, the natural alcohols according to the present invention are therefore usable in numerous applications.

According to a preferred embodiment of the invention, the natural fatty alcohols produced from the reduction of a vegetable or animal oil act as a solvent or co-solvent in a perfuming composition. In fact, these constituents advantageously solubilise all types of perfuming ingredients.

The fatty alcohols according to the invention can be used as solvents both in a perfuming composition comprising, in addition to the perfume, additives and adjuvants depending upon the final application, and in a concentrated perfume or base composition comprising only perfuming starting materials. The solvents generally used in these latter compositions, namely diethyl phthalate or dipropylene glycol, are suitable solvents for dissolving all the starting materials, both liquid and solid. However, we discovered, quite surprisingly, that the fatty alcohols according to the invention were also able to dissolve these substances and thus replace in particular the diethyl phthalate or dipropylene glycol.

The invention also relates to a perfuming composition, characterised in that it contains a fatty alcohol obtainable by the reduction process described in U.S. Pat. No. 5,831,133 or WO 99/12877.

In a particularly advantageous embodiment of the invention, the natural fatty alcohol present in a perfuming composition according to the invention advantageously replaces, in whole or in part, the solvent generally used. It therefore acts either as sole solvent or as co-solvent in combination with ethyl alcohol, isododecane or other solvents known to the skilled person and used in this type of composition. In this way, the proportion of ethanol, for example, can be reduced, even eliminated.

Furthermore, in applications such as perfumed massage oils which contain, in addition to the perfuming ingredients, paraffin oil (or an equivalent), the compounds according to the invention, owing to their structure, advantageously enable the perfume to be solubilised in the oil. This property of the fatty alcohols renders them highly useful in any type of perfuming composition containing an oil such as paraffin oil. Indeed, they preserve the properties of the natural oils from which they are derived whilst solubilising all the ingredients of the composition.

The perfuming composition according to the invention can contain, in addition to a fatty alcohol derived from an oil of natural origin and a perfuming ingredient, a volatile agent.

Preferred volatile agents in the perfuming composition according to the invention are the volatile hydrocarbons, the volatile silicone oils, isopentane or a mixture of these compounds. These are given as non-limiting examples, the skilled person being capable of selecting appropriate volatile agents other than those mentioned.

The skilled person is also capable of selecting one or more perfuming ingredients according to the nature of the product to be perfumed and the desired olfactory effect. These perfuming ingredients can belong to classes as varied as the alcohols, aldehydes, ketones, esters, ethers, acetates, nitrites, terpene hydrocarbons, nitrogenous or sulphurous heterocyclic compounds and also essential oils of natural or synthetic origin. Many of these ingredients are also listed in works of reference such as the book by S. Arctander, Perfume and Flavor Chemicals, 1969, Montclair, N.J., USA, or its more recent versions, or in other works of a similar nature.

Apart from the different types of ingredient mentioned, the perfuming composition according to the invention can also comprise other adjuvants such as antioxydants, chelating agents or propellants, the skilled person being capable of selecting them on the basis of the desired final application or the type of packaging used for the composition according to the invention.

Furthermore, according to a preferred embodiment of the invention, the perfuming composition comprises a fatty alcohol as mentioned hereinabove in combination with a natural oil (for example olive oil or sunflower oil). Thus combined, we discovered that the fatty alcohols obtained by reduction of a vegetable or animal oil of natural origin were, in fact, capable of reducing the greasy, sticky effect on the skin of the compositions containing fatty oils of natural origin. The presence of isopentane or other volatile hydrocarbons also has this effect.

The proportions in which the compounds according to the invention can be incorporated into the different aforementioned products varies within a wide range of values. These values depend on the role played by the fatty alcohols in the composition, i.e sole solvent or co-solvent. They also depend on the proportion of perfuming ingredient to be solubilised, i.e. indirectly on the nature of the perfuming composition and the desired olfactory effect.

As an example, typical proportions are in the order of 0.5% to 80%, preferably 10% to 40%, of fatty alcohol relative to the weight of perfuming composition into which it is incorporated.

By reason of their emollient properties, their non-greasy nature and their soft feel, they render the perfume or perfuming composition very pleasant to the touch when applied to the skin.

The invention will now be described in further detail in the following examples in which the abbreviations have the usual meaning in the art.

EXAMPLE 1

Preparation of Fatty Alcohols Derived from Animal or Vegetable Oils of Natural Origin The fatty alcohols according to the invention were all prepared by the following general method:

General Method

The fatty alcohols listed in Table I were prepared by reduction of vegetable and animal oils by injecting PMHS (2 equivalents per ester function) over the substrate containing the metal catalyst, in particular zinc (0.5–2 mol %) in solution in toluene, isopropyl ether or methyl-tert-amyl ether. At the end of the reaction, the polysilyl ether formed was hydrolysed over an aqueous solution of potash (1.2 eq KOH/mol of PMHS). After decanting, the organic solution was evaporated for recovery of the solvent, and the residue was distilled under vacuum to produce the alcohol in practically pure form with chemical yields generally exceeding 90%.

About twenty vegetable and animal oils were thus reducible to fatty alcohols using $Zn(dimethylacetate)_2$ (dimethylaminoethanol) as zinc catalyst with excellent chemical yields, as shown in Table I hereinafter. These alcohols correspond exactly, in their relative proportions and their stereochemistry, to the precursors fatty esters and triglycerides.

Other usable metal catalysts, in particular zinc catalysts, are described in detail in WO 99/12877 and the content of this document is included herein by reference. Identical products were obtainable by using the process described in U.S. Pat. No. 5,831,133 and the metal catalysts described therein, in particular $(2-ethylhexanoate)_2Zn$.

EXAMPLE 2

Perfuming Composition

A perfuming composition was prepared by mixing the following ingredients:

| Ingredients | Parts by weight |
|---|---|
| Isododecane | 39.800 |
| Fatty alcohol of soya[1] | 30.000 |
| Tenox ® GT-2[2] | 0.100 |
| Irganox ® PS-800[3] | 0.050 |
| Diethyl citrate[4] | 0.050 |
| Perfume[5] | 10.000 |
| Isopentane | 20.000 |
| Total | 100.000 |

[1] see Table I
[2] tocopherol; origin: Eastman
[3] dilauryl thiodipropionate; origin: Ciba Speciality Chemicals
[4] origin: Morflex
[5] the perfume was obtained by mixing the following ingredients:

| Ingredients | Parts by weight |
|---|---|
| Benzyl acetate | 92 |
| Dimethyl benzyl carbinyl acetate | 6 |
| Linalyl acetate | 10 |
| Benzyl alcohol | 50 |
| Phenylethyl alcohol | 35 |
| Amylcinnamic aldehyde | 24 |
| $C_{14}$ aldehyde at 10%* | 8 |

TABLE I

Composition and yields of the fatty alcohol obtained by reduction of the oil listed

| Vegetable or animal oil | $<C_{10}$ | $C_{10}$ | $C_{12}$ | $C_{14}$ | $C_{16}$ | $C_{18}$ | $C_{18:1}$ | $C_{18:2}$ | $C_{18:3}$ | $C_{20:1}$ | $C_{22:1}$ | $C_{24:1}$ | Density | Refractive index | Yeild (weight) | Yeild (mol) |
|---|---|---|---|---|---|---|---|---|---|---|---|---|---|---|---|---|
| Coconut | 6.9 | 5.9 | 48.8 | 19.3 | 7.1 | 1.3 | 0 | 2.1 | 0 | 0 | 0 | 0 | 0.8402 | 1.4435 | 83.7 | 94.0 |
| Palm | 3 | 3.2 | 50.2 | 16.5 | 8.1 | 1.6 | 11.0 | 1.2 | 0 | 0.2 | 0 | 0 | 0.8428 | 1.4453 | 78.2 | 90.7 |
| Cottonseed | 0 | 0 | 0 | 1 | 29.2 | 1.8 | 18.5 | 39.8 | 0 | 0 | 0 | 0 | Solid | — | 62.0 | 69.6 |
| Cocoa butter | 0 | 0 | 0 | 0 | 38.4 | 37.6 | 15.6 | 0.0 | 0 | 1.0 | 0 | 0 | Solid | — | 78.6 | 91.2 |
| Peanut | 0 | 0 | 0 | 0 | 12.3 | 2.2 | 45.4 | 21.7 | 0 | 0.4 | 0 | 0 | 0.8762 | 1.4620 | 84.1 | 94.4 |
| Almond | 0 | 0 | 0 | 0 | 8.0 | 1.1 | 62.9 | 25.5 | 0 | 0 | 0 | 0 | 0.8527 | 1.4611 | 84.4 | 94.7 |
| Colza | 0 | 0 | 1.6 | 0 | 10.6 | 6.4 | 71.6 | 2.3 | 0 | 0 | 0 | 0 | 0.8553 | 1.4657 | 56.3 | 63.2 |
| Olive | 0 | 0 | 0.2 | 0 | 14.5 | 2.4 | 72.6 | 7 | 0 | 0 | 0 | 0 | 0.8507 | 1.4586 | 73.5 | 82.3 |
| Sesame | 0 | 0 | 0 | 0 | 10.2 | 5.6 | 41.3 | 37.8 | 0 | 0 | 0 | 0 | 0.8516 | 1.4621 | 82.0 | 91.8 |
| Soya | 0 | 0 | 0 | 0.2 | 13.3 | 2.9 | 19.7 | 38.6 | 2.2 | 0 | 0 | 0 | 0.8533 | 1.4654 | 61.1 | 68.6 |
| Grapeseed | 0 | 0 | 0.5 | 0 | 8.2 | 3.4 | 19.4 | 44.5 | 0 | 0 | 0 | 0 | 0.8550 | 1.4668 | 75.5 | 84.7 |
| Corn | 0 | 0 | 0 | 0 | 11.6 | 1.5 | 29.8 | 48.6 | 0 | 0 | 0 | 0 | 0.8533 | 1.4642 | 74.6 | 83.2 |
| Sunflower | 0 | 0 | 0 | 0 | 11.0 | 5.3 | 27.8 | 55.8 | 0 | 0 | 0 | 0 | 0.8647 | 1.4665 | 69.4 | 80.5 |
| Safflower | 0 | 0 | 0 | 0.1 | 9.5 | 1.9 | 15.2 | 56.5 | 0 | 0 | 0 | 0 | 0.8567 | 1.4662 | 74.0 | 83.0 |
| Nut | 0 | 0 | 0 | 0 | 8.8 | 2.3 | 14.8 | 53.8 | 6 | 0 | 0 | 0 | 0.8659 | 1.4683 | 71.4 | 81.1 |
| Linseed | 0 | 0 | 0 | 0 | 6.1 | 3.3 | 19.7 | 11.6 | 58.2 | 0.2 | 0 | 0.2 | 0.8688 | 1.4708 | 64.6 | 74.9 |
| Jojoba | 0 | 0 | 1.9 | 0 | 0.8 | 0 | 0.0 | 6.9 | 0 | 58.2 | 25.0 | 3.7 | 0.8557 | 1.4610 | 86.2 | 95.0 |
| Butter | 1.7 | 5.8 | 7.5 | 23.9 | 31.9 | 4.5 | 2.2 | 10.1 | 1 | 0 | 0 | 0 | Solid | — | 13.8 | 21.2 |
| Pork | 0 | 0 | 0 | 1.9 | 30.0 | 14.2 | 36.2 | 8.7 | 0 | 0 | 0 | 0 | Solid | — | 79.3 | 86.8 |
| Cod liver | 0 | 0 | 0 | 6.7 | 17.1 | 3.5 | 17.7 | 3.7 | 1.3 | 8.8 | 6.8 | 0.0 | 0.8603 | 1.4697 | 77.2 | 83.2 |

$C_{10}$ = 1-decanol (capric alcohol)
$C_{12}$ = 1-dodecanol (lauryl alcohol)
$C_{14}$ = 1-tetradecanol (myristyl alcohol)
$C_{16}$ = 1-hexadecanol (cetyl alcohol)
$C_{18}$ = 1-octadecanol (stearyl alcohol)
$C_{18:1}$ = (9Z)-octadecen-1-ol (oleyl alcohol)
$C_{18:2}$ = (9Z,12Z)-octadecadien-1-ol(linoleyl alcohol)
$C_{18:3}$ = (9Z,12Z,15Z)-octadecatrien-1-ol(indenyl alcohol)
$C_{20:1}$ = (11Z)-eicosen-1-ol
$C_{22:1}$ = (13Z)-docosen-1-ol
$C_{24:1}$ = (15Z)-tetracosen-1-ol -continued

| Ingredients | Parts by weight |
|---|---|
| α-Ionone | 8 |
| Methyl anthranilate | 10 |
| Fatty alcohol of sunflower | 500 |
| Benzyl butyrate | 10 |
| Dihydrojasmone at 1%* | 17 |
| Habanolide ®[1] | 8 |
| Hedione ®[2] | 100 |
| Indole at 10%* | 10 |
| Linalol | 30 |
| Mayol ®[3] | 52 |
| Benzyl propionate | 16 |
| Benzyl salicylate | 14 |
| Total | 1000 |

*in dipropylene glycol (DIPG)
[1] pentadecenolide; origin: Firmenich SA, Geneva, Switzerland
[2] methyl dihydrojasmonate; origin: Firmenich SA, Geneva, Switzerland
[3] cis-7-p-menthanol; origin: Firmenich SA, Geneva, Switzerland Naturally, other perfuming ingredients can be used according to the desired odoriferous effect.

The natural alcohol of soya, together with isodecane, constitutes the solvent of this perfuming composition, which has a jasmine-type fragrance and imparts a soft, non-greasy feel when applied to the skin and at the same time perfumes it.

EXAMPLE 3
Perfuming Composition

A perfuming composition was prepared by mixing the following ingredients:

| Ingredients | Parts by weight |
|---|---|
| Isododecane | 24.800 |
| Fatty alcohol of soya[1] | 30.000 |
| Tenox ® GT-2[2] | 0.100 |
| Irganox ® PS-800[3] | 0.050 |
| Diethyl citrate[4] | 0.050 |
| Perfume[5] | 25.000 |
| Isopentane | 20.000 |
| Total | 100.000 |

[1] see Table I
[2],[3],[4] see Example 2
[5] the perfume used has the same composition as that described in Example 2

In this perfuming composition not containing ethanol, the soya alcohol acts as co-solvent. It solubilises perfectly the perfume used and makes the composition very pleasant to apply to the skin, softening it, but without making it greasy.

EXAMPLE 4
Perfuming Composition

A perfuming composition was prepared by mixing the following ingredients:

| Ingredients | Parts by weight |
|---|---|
| Ethanol at 96° | 29.800 |
| Fatty alcohol of olive[1] | 20.000 |
| Tenox ® GT-2[2] | 0.100 |
| Irganox ® PS-800[3] | 0.050 |
| Diethyl citrate[4] | 0.050 |

| Ingredients | Parts by weight |
|---|---|
| Perfume[5] | 30.000 |
| Isopentane | 20.000 |
| Total | 100.000 |

[1] see Table I
[2],[3],[4] see Example 2
[5] the perfume used has the same composition as that described in Example 2.

In this composition, the natural alcohol of olive replaces some of the ethanol at 96°. While preserving the properties of the natural olive oil, it solubilises the perfume used in a high concentration. In this way, a perfume is obtained which makes the skin soft and pleasant to touch.

EXAMPLE 5

Perfuming Composition

A perfuming composition was prepared by mixing the following ingredients:

| Ingredients | Parts by weight |
|---|---|
| Ethanol at 96° | 64.800 |
| Fatty alcohol of sesame[1] | 25.000 |
| Tenox ® GT-2[2] | 0.100 |
| Irganox ® PS-800[3] | 0.050 |
| Diethyl citrate[4] | 0.050 |
| Perfume[5] | 10.000 |
| Total | 100.000 |

[1] see Table I
[2],[3],[4] see Example 2
[5] the perfume used has the same composition as that described in Example 2.

The natural alcohol of sesame is used as co-solvent with ethanol. It allows the proportion of the latter in the composition to be reduced and imparts to it the characteristics of the natural oil, with the result that its application to the skin makes the skin very soft to the touch.

EXAMPLE 6

Perfumed Massage Oil

A perfuming composition for a massage oil was prepared by mixing the following ingredients:

| Ingredients | Parts by weight |
|---|---|
| Fatty alcohol of sunflower[1] | 5.000 |
| Vaseline oil | 45.000 |
| Witconol EC 1127[2] | 2.500 |
| Hostaphat KL 340 N[3] | 2.000 |
| Zetesol 100[4] | 39.800 |
| Mackalene 16[5] | 0.500 |
| Comperlan KD[6] | 3.000 |
| Kathon ® CG[7] | 0.100 |
| Tenox ® GT-2[8] | 0.500 |

-continued

| Ingredients | Parts by weight |
| --- | --- |
| Irganox ® PS-800[9] | 0.100 |
| Perfume[10] | 1.500 |
| Total | 100.000 |

[1] see Table I
[2] $C_{12}$–$C_{14}$ monoalkylethercitrate; origin: Witco Surfactants
[3] trilaureth-4-phosphate; origin: Clariant
[4] MIPA-laureth sulphate and laureth 4 cocamide DEA; origin: Zschimmer & Schwartz
[5] ricinoleamidopropyl dimethylamine lactate; origin: Mcintyre
[6] cocamide DEA; origin: Henkel
[7] methylchloroisothiazolinone and methylisothiazolinone; origin: Rohm & Haas
[8] tocopherol; origin: Eastman
[9] dilauryl thiodipropionate; origin: Ciba Speciality Chemicals
[10] the perfume used has the same composition as that described in Example 2.

The fatty alcohol of sunflower solubilises perfectly all the ingredients of this composition. The oil obtained penetrates easily when applied to the skin which, after application of said oil, remains very soft to the touch without being greasy.

In a variation on this composition, a mixture was prepared which comprised 90% of the massage oil of which the composition is described hereinabove and 10% of isopentane. A "post-foam" product was thus obtained which is applied to damp skin like a cream. By rubbing the skin, the product forms a foam which simply needs to be rinsed off. After application, the skin is soft and clean without being greasy.

EXAMPLE 7

Perfuming Composition for a Stick Deodorant

A perfuming composition for use in a stick deodorant was prepared by mixing the following ingredients:

| Ingredients | Parts by weight |
| --- | --- |
| Dow Corning 345 fluid[1] | 46.000 |
| Lorol C18[2] | 21.000 |
| Ucon fluid AP[3] | 1.800 |
| Cutina HR[4] | 1.000 |
| Eutanol G[5] | 3.200 |
| Fatty alcohol of cottonseed[6] | 5.000 |
| Zirkonal P10[7] | 21.000 |
| Perfume[8] | 1.000 |
| Total | 100.000 |

[1] cyclomethicone; origin: Dow Corning
[2] stearyl alcohol; origin: Henkel
[3] butyl ether; origin: Amerchol
[4] hydrogenated castor oil; origin: Henkel
[5] octyl dodecanol; origin: Henkel
[6] see Table I
[7] aluminium zirconium trichlorohydrex; origin: Giulini
[8] the perfume used has the same composition as that described in Example 2.

Cyclomethicone, stearyl alcohol, butyl ether, hydrogenated castor oil, octyl dodecanol and natural alcohol of cottonseed were mixed, then heated to reflux. The mixture was stirred continuously at 70° C. until all the solids had dissolved, then aluminium zirconium trichlorohydrex was dispersed in the initial mixture and stirred well. Lastly, the perfume was added to the mixture, which was then poured into suitable containers at 55° C. The resulting deodorant is very soft and gentle on the skin. Its soft, non-greasy texture produces a very pleasant effect on the skin.

What is claimed is:

1. A perfuming composition consisting of a perfume concentrate and a fatty alcohol obtainable by a process which comprises reducing the carbonyl function of a vegetable or animal oil by reacting the vegetable or animal oil with appropriate quantities of polymethylhydroxy-siloxane (PMHS) in the presence of a catalytic system prepared from a metal salt or complex and a reducing agent, followed by hydrolysing the resulting siloxane with a basic agent and then separating and purifying the resulting fatty alcohol.

2. A perfuming composition according to claim 1, wherein the vegetable or animal oil is selected from the group consisting of olive oil, sunflower oil, palm oil, cottonseed oil, colza oil, soya oil, sesame oil, jojoba oil and coconut oil.

3. A perfuming composition according to claim 1, wherein the fatty alcohol is present in a proportion of between 0.5% and 80% of the composition.

4. A perfuming composition that includes a perfume concentrate and has a fatty alcohol as the only solvent in the composition.

5. The perfuming composition of claim 4, wherein the fatty alcohol is present in a proportion of between 0.5% and 80% of the composition.

6. The perfuming composition of claim 4, which includes an additive.

7. The perfuming composition of claim 6, wherein the additive is paraffin oil, an antioxidant, a chelating agent, or a propellant.

8. The perfuming composition of claim 4, in the form of a perfume, an eaux de toilette or an essential oil.

9. A perfuming composition consisting of a perfume concentrate and a fatty alcohol.

10. The perfuming composition of claim 9, wherein the fatty alcohol is obtained by a process which comprises reducing the carbonyl function of a vegetable or animal oil by reacting the vegetable or animal oil with appropriate quantities of polymethylhydroxy-siloxane (PMHS) in the presence of a catalytic system prepared from a metal salt or complex and a reducing agent, followed by hydrolyzing the resulting siloxane with a basic agent and then separating and purifying the resulting fatty alcohol.

11. The perfuming composition according to claim 9, wherein the vegetable or animal oil is selected from the group consisting of olive oil, sunflower oil, palm oil, cottonseed oil, colza oil, soya oil, sesame oil, jojoba oil and coconut oil.

12. The perfuming composition of claim 9, wherein the fatty alcohol is present in a proportion of between 0.5% and 80% of the composition.

13. The perfuming composition of claim 9, in the form of a perfume, an eaux de toilette or an essential oil.

\* \* \* \* \*

UNITED STATES PATENT AND TRADEMARK OFFICE
CERTIFICATE OF CORRECTION

PATENT NO. : 6,806,250 B2 Page 1 of 1
DATED : October 19, 2004
INVENTOR(S) : Mimoun et al.

It is certified that error appears in the above-identified patent and that said Letters Patent is hereby corrected as shown below:

<u>Title page,</u>
After Item [63], Related U.S. Application Data, please insert the following:
-- [30] Foreign Application Priority Data
    Nov. 10, 1999    (CH)................ 2058/99 --

Signed and Sealed this

Thirtieth Day of November, 2004

JON W. DUDAS
*Director of the United States Patent and Trademark Office*